(12) United States Patent
Kitajima et al.

(10) Patent No.: US 6,225,130 B1
(45) Date of Patent: May 1, 2001

(54) METHOD OF SEPARATING SERUM FROM WHOLE BLOOD

(75) Inventors: Masao Kitajima; Akemi Higo; Shigeru Tezuka, all of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/252,310

(22) Filed: Feb. 18, 1999

(30) Foreign Application Priority Data

Feb. 19, 1998 (JP) .................................................. 10-037606

(51) Int. Cl.[7] ...................................................... G01N 1/18
(52) U.S. Cl. ........................... 436/177; 436/16; 436/54; 436/69; 436/174; 422/73; 422/101; 210/645; 210/767; 210/808
(58) Field of Search ................................ 436/16, 54, 63, 436/69, 174, 177, 178, 180; 422/73, 100, 101; 210/637, 645, 650, 651, 767, 808, 455, 321.6

(56) References Cited

U.S. PATENT DOCUMENTS

| | | | |
|---|---|---|---|
| 4,477,575 | 10/1984 | Vogel et al. | 436/170 |
| 4,810,394 | * 3/1989 | Masuda | 210/767 |
| 5,139,685 | * 8/1992 | de Castro et al. | 210/767 |
| 5,423,989 | * 6/1995 | Allen et al. | 210/650 |
| 5,876,605 | * 3/1999 | Kitajima et al. | 210/650 |
| 5,979,669 | * 11/1999 | Kitajima et al. | 210/455 |
| 5,996,811 | * 12/1999 | Kitajima et al. | 210/488 |
| 6,045,699 | * 4/2000 | Yazawa et al. | 210/637 |

FOREIGN PATENT DOCUMENTS

| | | |
|---|---|---|
| 0 785 012 | 7/1997 | (EP) . |
| 0 785 430 | 7/1997 | (EP) . |
| WO 97/29369 | 8/1997 | (WO) . |

* cited by examiner

Primary Examiner—Maureen M. Wallenhorst
(74) Attorney, Agent, or Firm—Reed Smith LLP

(57) ABSTRACT

A method for separating serum from whole blood in a vessel at an insertion speed of 30 cm/sec or less and maintaining the suction pressure of the suction nozzle at 400 mm Hg or less. Improved analytical results are obtained because the serum can be produced without hemolysis.

7 Claims, 6 Drawing Sheets

METHOD OF SEPARATING SERUM FROM WHOLE BLOOD

BACKGROUND OF THE INVENTION

This invention relates to a method of preparing a serum sample from whole blood.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter unit composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1)

Another blood filter unit composed of a holder body and a cap was also developed. The holder body consists of a plasma receiver located on the upper side and a filter chamber located on the underside. The filter material put in the filter chamber is composed of six sheets of glass fiber filter and one sheet of polysulfone microporous membrane (Example 1 of EP 785012A1).

Incidentally, after drawing blood, fibrins gradually deposit to coagulate blood cells in whole blood samples, and as a result, agglutinates are formed, and serum is separated. Thereupon, serum can be obtained by sucking serum portion after agglutinates are formed.

While repeating analysis of the serum samples, the inventors found that, there is a dispersion of analytical results due to the destruction of blood cells caused by pressing agglutinates upon sucking the serum.

SUMMARY OF THE INVENTION

Accordingly, an object of the invention is to provide a method of preparing a serum sample from whole blood without destroying blood cells, and thereby, of obtaining highly reliable analytical values.

The inventors investigated eagerly in order to achieve the above object, and found that, there is a critical value between the insertion speed of a serum suction nozzle into a vessel and a suction pressure, and a blood serum sample can be obtained without destruction of blood cells by sucking the blood serum which keeping the sucktion pressure under the critical value.

Thus, the present invention provides a method of separating serum portion from whole blood which comprises inserting a suction nozzle provided with an agglutinate stopper at the lower and into whole blood wherein fibrins deposited placed in a vessel at an insertion speed of 30 cm/sec or less, and keeping the suction pressure of the suction nozzle at 400 mm Hg or less.

Holder body
Glass fiber filter chamber
Microporous membrane chamber
Inclined portion
Flange
Glass fiber filter-placing portion
Funnel-shaped disc portion
Blood inlet
Step portion
Cap
Outer wall
Inner wall
Cup
Flange
Rib
Projection
Filtrate passage
Pent roof
Discharge port
Glass fiber filter
Polysulfone microporous membrane
Suction nozzle
Step portion
Large diameter portion
Rib
Suction port
Agglutinate stopper
Grid
Upper disc
Lower disc
Netting
Truncated cone-shaped cylinder
Netting
Ring plate
Leg

DETAILED DESCRIPTION OF THE INVENTION

The whole blood applicable to the invention is any blood wherein agglutinates of blood cells are formed by the deposition of fibrins, and includes human blood and other animal bloods, whole blood, to which a sufficient amount of an anticoagulant, such as heparin, is added, is out of the scope of the invention, because of not forming agglutinates.

On the other hand, although coagulation is accelerated by adding a coagulation accelerator, such as polyvalent ion, e.g. Ca ion, inorganic compound, e.g. silica, or thrombin, the method of the invention is applicable, irrespective of the addition of coagulation accelerator. A suitable volume of whole blood varies according to the object of use, and in the case of dry analysis using an analytical element, a suitable volume is about 0.1 to 20 ml, usually about 1 to 10 ml.

An agglutinate stopper is attached to the end of the suction nozzle. The agglutinate stopper functions as a filter of serum which inhibits agglutinates from entering the suction nozzle, and has a liquid intake formed of a filter material, such as netting, grid, perforated plate, or slit(s), or any other member having a plurality of openings, such as pores. A suitable size (mesh) of a mean diameter of the filter material, such as netting or grid, is about 100 μm to 5 mm, preferably about 0.5 to 2 mm. It is effective to provide the liquid intake on the underside in addition to the bottom of the agglutinate stopper, and the whole area of the agglutinate stopper may be formed by one or more a filtering materials, such as netting. It is also effective to provide the liquid intake on the side of the suction nozzle and the attach a porous plastic disc or netting having a diameter slightly smaller than the inside diameter of the vessel for containing blood to the end of suction nozzle as the agglutinate stopper. By pushing down the porous disc or the netting into the vessel, agglutinates are forced to descend, and serum portion containing a small amount of blood cells remains on the upper side which is sucked through the liquid intake. Some examples of the agglutinate stopper are illustrated in FIGS. 6–10.

Figure 6:
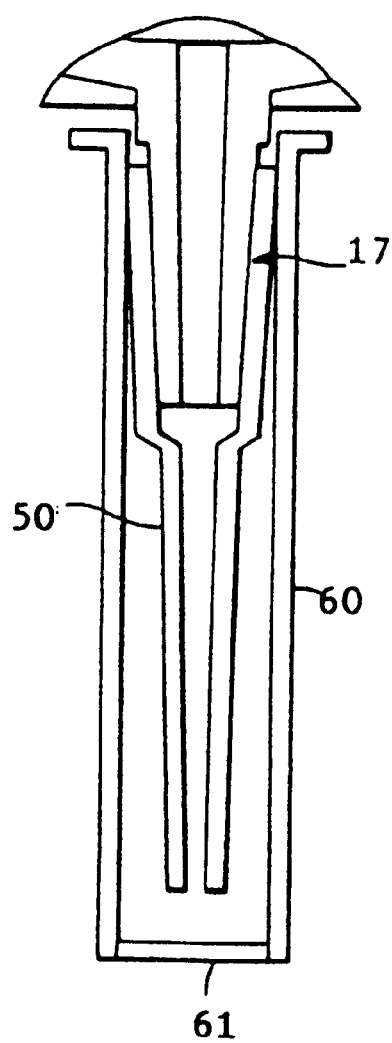
FIG. 6 is a longitudinal section of the blood inlet portion of the blood filter unit to which the suction nozzle and an agglutinate stopper are attached.
Figure 7:
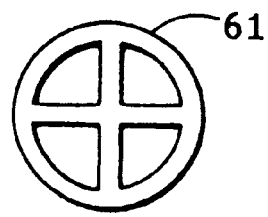
FIG. 7 is a bottom view of the agglutinate stopper.

The agglutinate stopper 60 of FIG. 6 is in the form of a cylinder, and a cross-shaped grid 61 shown in FIG. 7 is provided at the end opening.

Figure 8:
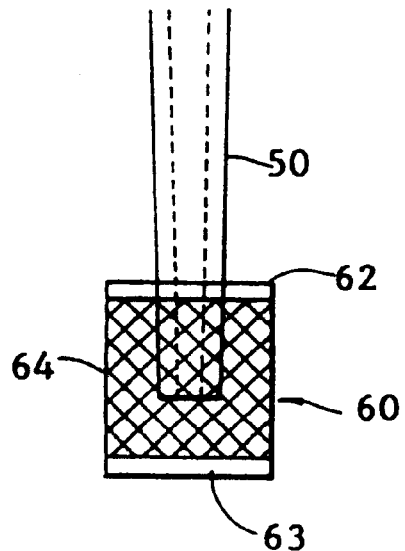
FIG. 8 is a side view of another agglutinate stopper.

The agglutinate stopper 60 of FIG. 8 is formed of an upper disc 62, a lower disc 63 and a netting 64 provided therebetween. A cicular hole is formed at the center of the upper disc 62, and the end of the suction nozzle 50 inserted thereinto is joined by welding.

Figure 9:
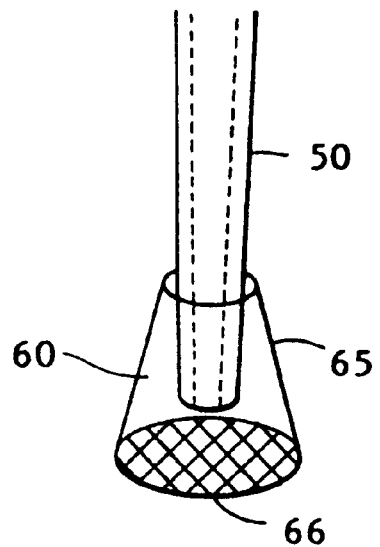
FIGS. 9 and 10 are perspective views of still other agglutinate stoppers.

The agglutinate stopper 60 of FIG. 9 is formed of a truncated cone-shaped cylinder 65 and a netting 66 provided on the bottom thereof. The suction nozzle 50 is inserted into the upper opening of the cylinder 65, and joined by welding.

Figure 10:
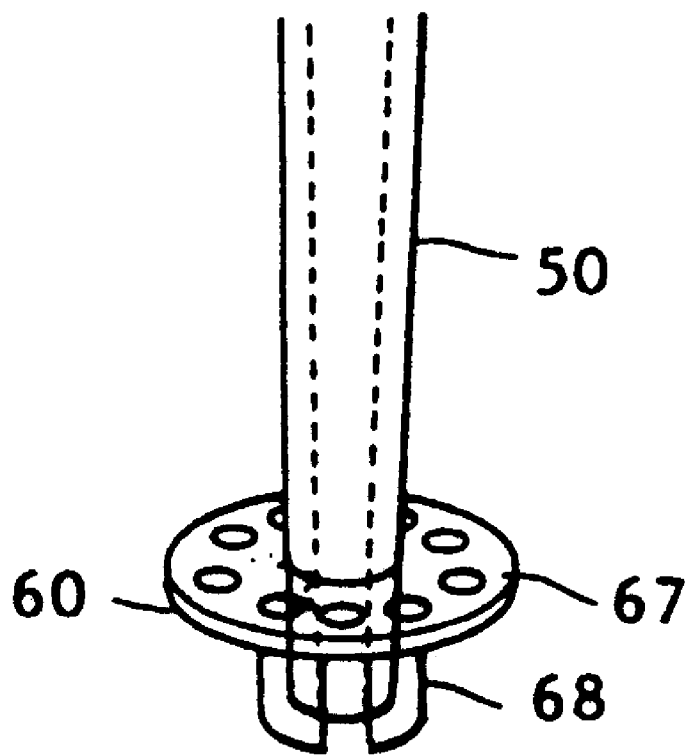

The agglutinate stopper 60 of FIG. 10 is in the form of a ring plate 67 provided with 9 circular holes at regular intervals. Two through-shaped legs 68 faced to each other are provided on the underside of the ring plate 67 at the inner periphery. The end of the suction nozzle 50 is fitted into the center hole of the ring plate 67, and caught by the legs 68.

One characteristic of the invention is the insertion speed of the suction nozzle provided with the agglutinate stopper into whole blood, and the speed is made 30 cm/sec or less, preferably 10 cm/sec or less, more preferably 5 cm/sec or less. The lower limit of the insertion speed depends on practical viewpoint, i.e. separation time of serum, and 0.2 cm/sec or more, preferably 1 cm/sec or more. Agglutinates are composed of fibrins deposited in the form of a netting and cellular components, such as erythrocytes, leukocytes and thrombocytes, incorporated thereinto, and are soft and tend to be broken. Accordingly, it is important to push down the agglutinate stopper slowly so as not to enter agglutinates. However, agglutinates may cross over the agglutinate stopper at the periphery where the agglutinates do not meet the agglutinate stopper. Besides, in the case of small agglutinates having a diameter of 15 mm φ or less which are dispersible, relative position of the stopper to the agglutinates does not become a problem.

The other characteristic of the invention is the serum suction pressure of the suction nozzle, and the suction pressure, i.e. pressure difference, is made 400 mm Hg or less, preferably 200 mm Hg or less. The lower limit of the suction pressure depends on practical viewpoint, i.e. separation time of serum, and 50 mm Hg or more, preferably 100 mm Hg or more.

The whole blood from which serum is separated is left in a vessel, and waits for the deposition of fibrins to form agglutinates. The vessel can be chosen from various vacuum blood collecting tube, sample tubes, test tubes, cups, and so on. The formation period of agglutinates varies by the presence of coagulation accelerator, respective humans and the like, and in the case of the absence of coagulation accelerator, the period is about 20 to 60 minutes after drawing blood. In the case of the presence of coagulation accelerator, the period is about 1 to 20 minutes. By leaving the whole blood longer than the above period, even if agglutinates are completely degenerated and separated into serum and cellular components, such a whole blood is still applicable to the invention. In any event, the method of the invention is particularly effective against the filtration of the whole blood wherein, although fibrins have been deposited, coagulation of blood does not proceed sufficiently, and the formation of agglutinates is insufficient. The whole blood in this state is, in general, after 1 to 30 minutes, especially about 1 to 20 minutes from the time of drawing blood, irrespective of the presence or absence of coagulation accelerator.

Since the serum poriton which is sucked by the suction nozzle through the agglutinate stopper contains cellular components in an amount of about 0.1 to 10% as hematocrit value, it is necessary to remove the cellular components by a blood filtering material. As a means of filtering the serum portion, a blood filter unit is applicable to which the suction nozzle is connected. In this case, the insertion speed of 30 cm/sec or less can be satisfied either by moving the suction nozzle or by moving the vessel containing blood.

A preferable blood filtering material comprises glass fiber filter and microporous membrane.

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 μm preferably 1 to 5 μm. By treating the surface of glass fiber with hydrophilic polymer as disclosed in Japanese Patent KOKAI Nos. 2-208676, 4-208856, filtration proceeds more fast and smoothly. Lectin or other reactive reagent or modifier may be incorporated into glass fiber, or glass fiber may be treated therewith. Two or more glass fiber filters may be laminated.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 μm or more, preferably about 0.3 to 5 μm, more preferably about 0.5 to 4.5 μm, particularly preferably about 1 to 3 μm. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, etc. The surface of the membrane may be hydrolyzed or may be rendered hydrophilic by a hydrophilic polymer or an activating agent.

As the fluorine-containing polymer membrane, there are the microporous matrix membrane (microporous layer) composed of polytetrafluoroethylene fibrils (fines) disclosed in WO 87/02267, Gore-Tex (W. L. Gore and Associates), Zitex (Norton), Poreflon (Sumitomo Denki), etc. Other fluorine-containing polymer sheets usable as the microporous layer include polytetrafluoroethylene microporous membranes disclosed in U.S. Pat. No. 3,368,872 (Examples 3 and 4), U.S. Pat. No. 3,260,413 (Examples 3 and 4), U.S. Pat. No. 4,201,548, etc., polyvinylidenefluoride microporous membranes disclosed in U.S. Pat. No. 3,649,505 and the like.

It is wellknown that fluorine-containing polymer microporous membranes as it is have a low surface tension. As a result, when the membrane is used as the blood cell filtering layer, aqueous liquid samples are repelled and do not diffuse nor permeate over the surface or into the inside. In the invention, the above repelling problem has been resolved by incorporating a sufficient amount of surfactant for rendering the outer surface and the inner space surface of the fluorine-containing polymer microporous membrane substantially hydrophilic thereinto.

As the surfactant for rendering the fluorine-containing polymer microporous membrane hydrophilic, the surfactant may be nonionic, anionic, cationic or ampholytic. However, nonionic surfactants are advantageous for the multilayer analytical elements for analyzing whole blood samples, because nonionic surfactants have a relatively low hemolytic activity among the above surfactants. Suitable nonionic surfactants include alkylphenoxypolyethoxyethanol, alkylpolyether alcohol, polyethyleneglycol monoester, polyethyleneglycol diester, higher alcohol-ethylene oxide adduct (condensate), polyol ester-ethylene oxide adduct (condensate), higher fatty acid alkanol amide, etc.

The fluorine-containing polymer microporous membrane may be rendered hydrophilic by providing one or more water-insolubilized water-soluble polymers in its porous spaces. The water-soluble polymers include oxygen-containing hydro carbons, such as polyacrylamide, polyvinylpyrrolidone, polyvinylamine and polyethylenamine, negative charge-containing ones such as polyvinyl alcohol, polyethylene glycol, methyl cellulose, ethyl cellulose, hydroxyethyl cellulose and hydroxypropyl cellulose, nitrogen-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like. Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide, N-methyl-2-pyrolidone or a mixed solvent thereof to obtain a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-012640, 56-86941, 56-154051, etc., and they are applicable to the invention. The polysulfone microporous membrane can be rendered hydrophilic, similar to the fluorine-containing polymer, by incorporating surfactant or providing water-insolubilized water-soluble polymer.

As the other nonfibrous microporous membranes, blushed polymer membranes composed of a cellulose ester, such as cellulose acetate, cellulose acetate/butyrate or cellulose nitrate, disclosed in U.S. Pat. No. 3,992,158 or U.S. Pat. No. 1,421,341 are preferable. Microporous membranes of polyamide, such as 6-nylon or 6,6-nylon, or polyethylene, polypropylene, or the like are also usable. Other nonfibrous microporous membranes usable include continuous microspace-containing porous membranes where polymer particulates, glass particulates, diatomaceous earth or the like are joined by a hydrophilic or non-water-adsorptive polymer, such as disclosed in U.S. Pat. No. 3,992,158, and U.S. Pat. No. 4,258,001.

Suitable effective pore size of the nonfibrous microporous membrane is 0.2 to 10 $\mu$m, preferably 0.3 to 5 $\mu$m, particularly preferably 0.5 to 5 $\mu$m. The effective pore size of the nonfibrous porous membrane in the invention is the pore size measured by the bubble point method according to ASTM F316-70. In the case that the nonfibrous porous membrane in a membrane filter composed of blushed polymer prepared by the phase separation method, the liquid passages in the thickness direction are, in general, the narrowest at the free surface (glossy face) in the manufacturing process of the membrane, and the pore size in section of each liquid passage stipulated a circle is the smallest near the free surface. The minimum pore size of passages in the thickness direction per unit area has a distribution in facial direction of the membrane filter, and the maximum value determines filtration performance. In general, it is determined by the limit bubble point method.

As mentioned above, in the membrane filter composed of blushed polymer prepared by the phase separation method, liquid passages in the thickness direction become the narrowest at the free surface (glossy face) in the manufacturing process of the membrane. In the case of using the membrane as the nonfibrous porous membrane of the filtering material of the invention, it is preferable to face the glossy face of the membrane filter toward the side to discharge the plasma portion.

A third filtering material may be incorporated into the blood filtering material. The third filtering material may be filter paper, nonwoven fabric, woven fabric such as plain weave fabric, knitted fabric such as tricot fabric, etc. Among them, woven fabric and knitted fabric are preferred. The woven fabric or the like may be treated by glow discharge as disclosed in Japanese Patent KOKAI No. 57-66359. The third filtering material is preferably interposed between the glass fiber filter and the microporous membrane.

Preferable microporous membranes are polysultone membrane, cellulose acetate membrane and the like, and particularly preferred one is polysulfone membrane. In the blood filtering material of the invention, the glass fiber filter is located on the blood inlet side and the microporous membrane in located on the filtrate outlet side. The most preferable blood filtering material is a laminate of the glass fiber filter and polysulfone membrane laminated in this order from the blood inlet side.

Respective layers may be integrated by joining each other using partially disposed (e.g. spots) adhesive, according to disclosures in Japanese Patent KOKAI Nos. 62-138756-8, 2-105043, 3-16651, etc.

In the filtering material of the invention, it is though that the filter material does not trap blood cells only by the surface, but catches to remove blood cells gradually by entangling at first large blood cell components and then smaller blood cell components in the space structure with permeating in the thickness direction in total of the filtering material, called the volumetric filtration.

The quantity of whole blood filterable by this system is greatly influenced by the void volume existing in glass fiber filter and the volume of blood cells in the whole blood. When the density of the glass fiber filter is high (pure size to retain particles is small), erythrocytes are trapped in the vicinity of glass fiber filter surface, voids in the glass fiber filter are clogged in a very thin region from the surface, and accordingly, filtration does not proceed thereafter. As a result, recovered plasma volume by filtration is small. On that occasion, when the filter material is sucked by stronger suction in order to increase recovered plasma volume, blood cells are destroyed, i.e. hemolyzed. That is, the filtration becomes similar to surface filtration, and utilization rate of void volume of the filter is low.

As an indicator corresponding to void volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking at a constant pressure. The water permeation speed is filtrate volume per unite area and time, and expressed by ml/sec.

For example, glass fiber filter 20 mm φ in diameter is put in a filter unit, and a 100 ml syringe containing 60 ml water is connected to the top of the filter unit. Water flows down naturally, and volume of water passing through the glass fiber filter from 10 sec to 40 sec after starting is measured as the water permeation volume, and the water permeation speed per unit area is calculated from it.

Glass fiber filters particularly suitable for plasma separation are having a water permeation speed of about 1.0 to 1.3 ml/sec, and illustrative of the glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 g/cm$^3$) on a nylon net. The glass fiber filter thus prepared shows good plasma separating ability.

A suitable thickness of the glass fiber filter varies according to the plasma volume to be recovered and density (void content) and area of the glass fiber filter. A necessary amount of plasma for analyzing plural items using dry analytical elements is 100 to 500 μl. In practical viewpoint, a glass fiber filter having a density of about 0.02 to 0.2 g/cm$^3$ and an area of 1 to 5 cm$^2$ is suitable. In this case, a suitable thickness of the glass fiber filter is about 1 to 10 mm, preferably about 2 to 8 mm, more preferably about 4 to 6 mm. The above thickness can be made by superposing 1 to 10 sheets, preferably 2 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

In the case of blood filter unit, the blood filtering material is placed in a holder having a blood inlet and a plasma outlet. The holder is, in general, formed of a body accommodating the blood filtering material and a cap, and each of them is provided with at least one aperture. One is used as the blood inlet, and the other is used as the plasma outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which accommodates the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material.

Besides, it is preferable that the periphery of the blood filtering material is closely fitted to the wall of the filter chamber so as not to form a bypass of whole blood without passing the filtering material.

The blood filter unit is made into a closed structure except the blood inlet and the plasma outlet by attaching a cap to the holder body.

As the material of the holder, thermoplastic or thermosetting plastics are preferable. Illustrative of the plastics are general-purpose plystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss.

The filtration of the sucked serum portion is carried out by supplying the serum portion to the opening on the glass fiber filter side of the holder, and sucking from the opening on the opposite side to collect the filtrate which is serum. A suitable supply volume of the serum portion is about 1.2 to 5 times, preferably about 2 to 4 times that of the blood filtering material. During filtering, pressure may be applied from the supply port.

EXAMPLES

Example 1

Figure 1:
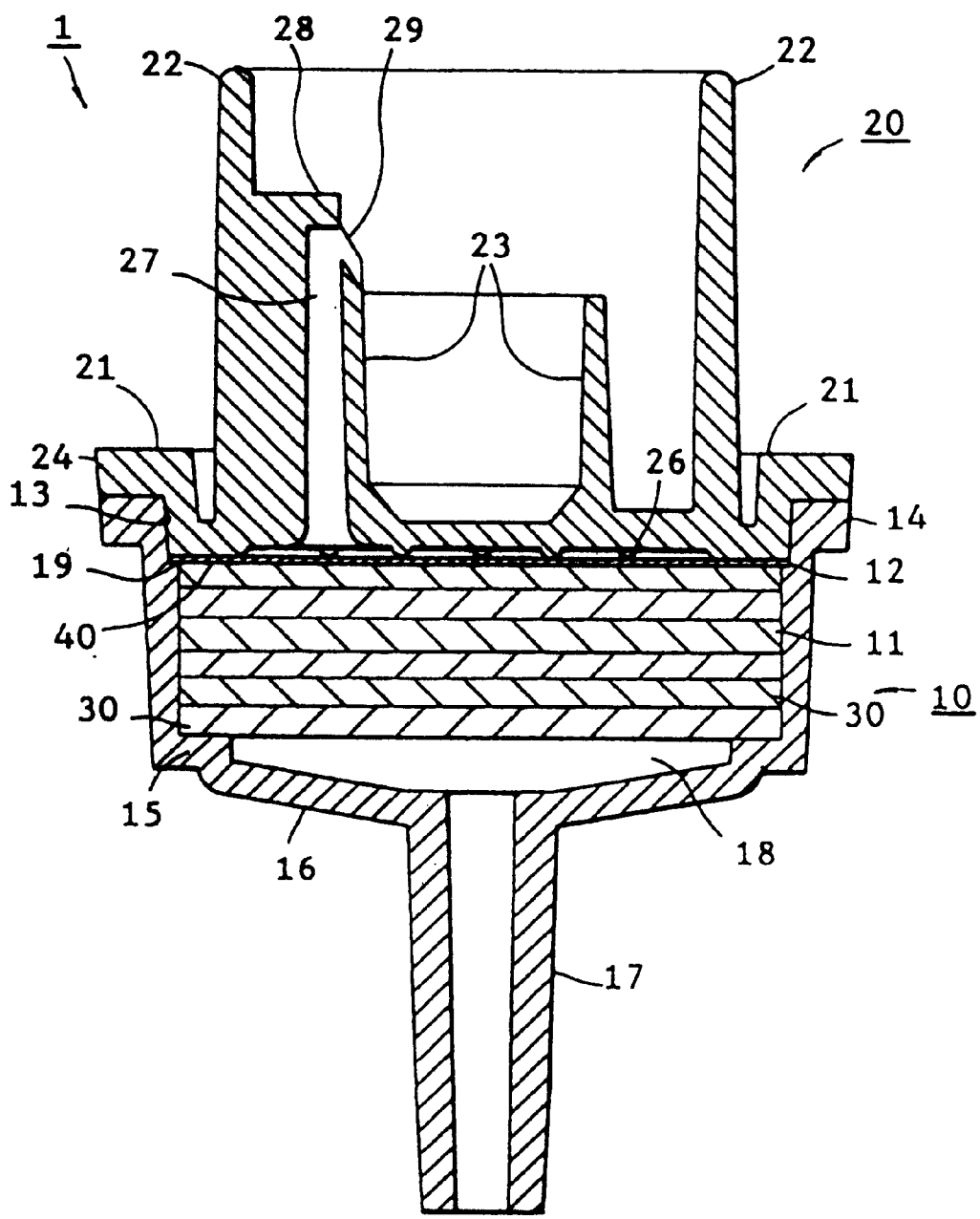
FIG. 1 is a longitudinal section of a blood filter unit used in the examples of the invention.
Figure 2:
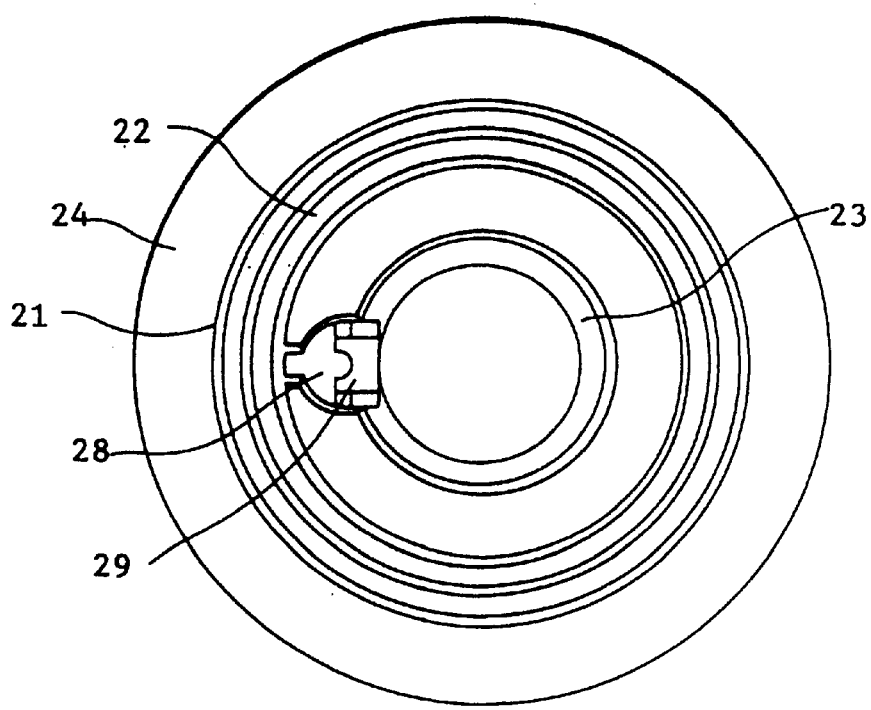
FIG. 2 is a plan view of the cap of the unit.
Figure 3:
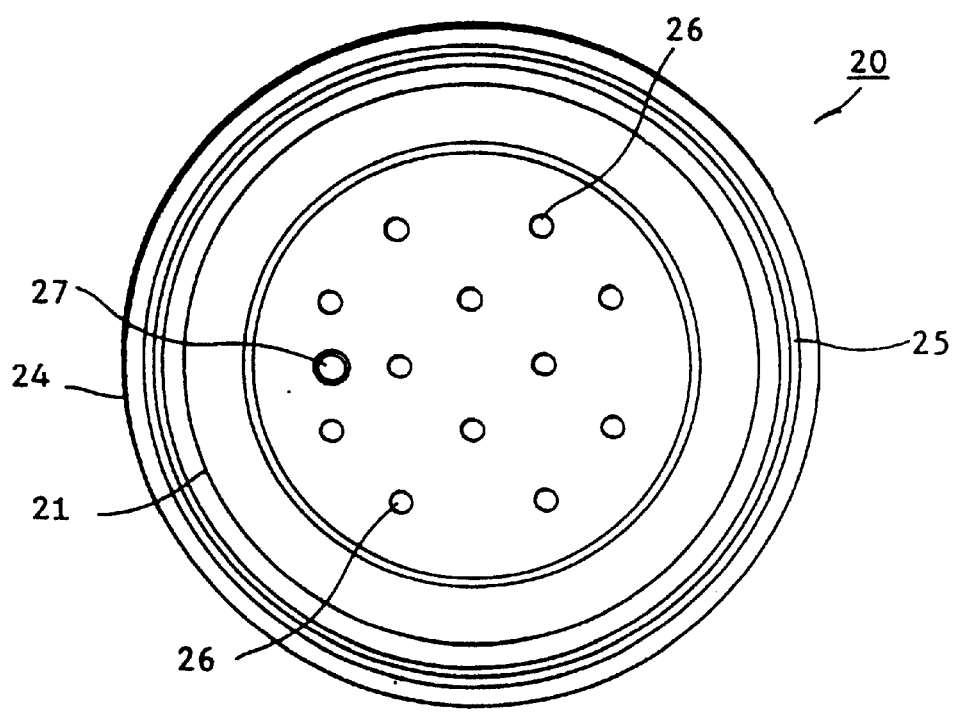
FIG. 3 is a bottom view thereof.

A blood filter unit illustrated in FIGS. 1–3 was prepared. FIG. 1 is a longitudinal section of the blood filter unit in the assembled state, FIG. 2 is a plan view of the cap which constitutes the blood filter unit, and FIG. 3 is a bottom view thereof.

The blood filter unit is, as shown in FIG. 1, composed of a holder 1 consisting of a holder body 10 and a cap 20 and blood filtering material consisting of a glass fiber filter 30 and a microporous membrane 40.

The holder body 10 is made of high-impact polystyrene resin, and has a glass fiber filter chamber 11 for containing the glass fiber filter 30 and a microporous membrane chamber 12 for containing a polysulfone microporous membrane as the microporous membrane 40 above the glass fiber filter chamber 11. The microporous membrane has a diameter greater than the glass fiber filter chamber, and the periphery of the microporous membrane 40 is nipped by the step portion 19 formed on the foundary between the glass fiber filter chamber 11 and the microporous membrane chamber 12 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the other hand, the bottom of the holder body 10 is in the form of a shallow funnel, and a step portion is formed as a glass fiber filter-placing portion 15 at the periphery of the funnel-shaped disc portion 16. A nozzle-shaped blood inlet 17 is formed downward as the supply port of liquid to be filtered at the center of the funnel-shaped disc portion 16. A suction nozzle (not illustrated) is fitted to the nozzle-shaped blood inlet 17. The glass fiber filter-placing portion 15 also functions as a spacer which separates the glass fiber filter 30 from the bottom and forms a space 18 for spreading the liquid to be filtered over the whole surface of the glass fiber filter 30.

The cap 20 has an outer wall 21 and an inner wall 20 formed concentrically and a cup 23 as the receiver of the filtrate. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined 13 in a sealed state. A flange 24 is formed outward at the periphery of the outer wall 21, and the flange 24 is bonded to the flange 14 of the holder body 10 by ultrasonic welding. As shown in FIG. 3, a rib 25 is formed on the underside of the flange 24 so as to concentrate the ultrasonic energy there to be bonded to each other to ensure sealing. The rib 25 disappears after bonding.

As shown in FIG. 3, twelve projections 26 are formed at the bottom of the cap 20 at almost regular intervals. The projection 26 prevent the polysulfone microporous membrane 40 from adhering to the bottom.

A chimney-shaped filtrate passage 27 is formed upward penetrating the bottom of the cap 20, and a pent roof 28 is formed horizontally at the upper end of the filtrate passage 27 so as to prevent spouting of the filtrate. The pent roof 28 has the form of a combination of two half circles, as shown in FIG. 2, and the periphery of the large half circle conforms to the periphery of the filtrate passage 27. The periphery of the filtrate passage 27. The discharge port 29 of the filtrate is provide obliquely at the upper end of the filtrate passage 27, and has the form of a lower half ellipse.

The above blood filter unit has a diameter of the glass fiber filter chamber 11 of 20, 1 mm and a depth thereof of 5.9 mm, a diameter of the microporous membrane chamber 12 of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the cup 23 of 7.5 mm. The glass fiber filter 30 consists of six glass fiber filter sheets each having a diameter of 20.0 mm and a thickness of 0.91 mm, and the microporous membrane consists of one polysulfone microporous membrane having a diameter of 20.9 mm and a thickness of 150 μm.

Figure 4:
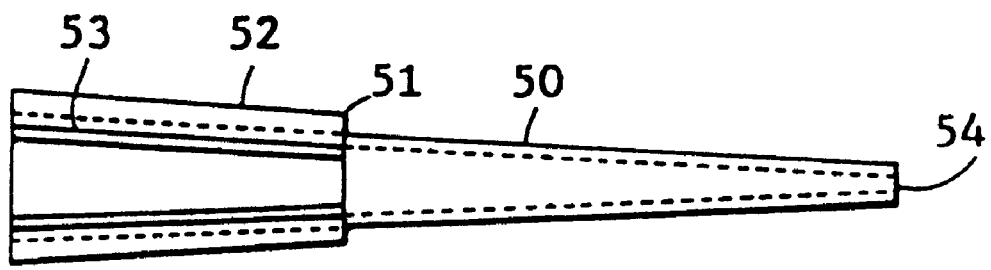
FIG. 4 is a side view of a suction nozzle attached to the blood inlet of the blood filter unit.
Figure 5:
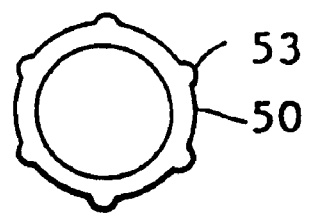
FIG. 5 is a plan view thereof.

A suction nozzle 50 as shown in FIGS. 4–5 is fitted to the nozzle-shaped blood inlet 17. The suction nozzle 50 is in the form of a slender truncated cone-shaped cylinder, and a step portion 51 is provided on the midway to render the diameter narrower. Six sibs 53 are formed on the outer periphery of the large diameter portion 52 in the axial direction. The end opening of the suction nozzle 50 is the suction port 54.

To the end of the suction nozzle 50, the agglutinate stopper 60 shown in FIG. 10 was attached. The agglutinate stopper 60 consisted of a ring plate 17 having a diameter of 10 mm at which 9 holes 1 mm in diameter were provided, and two trough-shaped legs 68 having a width of 1.5 cm and a length of 1 mm.

Four 5 ml vacuum blood collecting tubes for silica gel blood collection (Terumo, for serum) were provided.

A tube rack was put on an even balance, and a blood collecting tube containing 5 ml whole blood (hematocrit:43%) was put in the rack. After subtracting the tare weight, the above agglutinate stopper having a bottom area (except space) of about 3 cm$^2$ attached to the suction nozzle was pressed against agglutinate, and the indicated value of the valance at the time of breaking the agglutinate was recorded.

The above experiment was conducted after 30 minutes, 60 minutes, 90 minutes and 120 minutes from drawing blood, respectively.

The results are summarized in Table 1.

TABLE 1

| Time after Drawing Blood | Pressure upon Breaking Agglutinate |
| --- | --- |
| 30 min | 90 g/cm$^2$ |
| 60 min | 50 g/cm$^2$ |
| 90 min | 50 g/cm$^2$ |
| 120 min | 37 g/cm$^2$ |

Example 2

Two 9 ml silica gel vacuum blood collecting tubes (Terumo, for serum) were provided, and 9 ml whole blood (hematocrit: 39%) was placed in each blood collecting tube. The above agglutinate stopper attached to the suction nozzle having a weight of 50 g was inserted into the whole blood by its own weight at a speed of 5 cm/sec to the depth of 2 cm from the surface of the whole blood to suck serum portion. The suction filtration was conducted after 30 minutes and 60 minutes from drawing blood. The suction was carried out by using a peristaltic pump at a suction pressure (pressure difference) of 300 mm Hg at the maximum for a suction period of 15 seconds.

As a result, 300 μl of serum after 30 minutes and 1 ml of serum after 60 minutes were obtained. Meanwhile, the suction filtration could be continued without clogging the suction port by agglutinate.

Example 3

Four 5 ml thrombin blood collecting tubes ("Insepak", for serum, Sekisui Chemical Co., Ltd.) were provided, and 5 ml whole blood (hematocrit:39%) was placed in each blood collecting tube. The above agglutinate stopper attached to the suction nozzle was inserted into the whole blood at a suction pressure of 100 mm Hg at a speed of 10 cm/sec to about the center of the whole blood to suck serum portion. The suction filtration was conducted after 30 minutes and 60 minutes from drawing blood. The suction was (arried out by using a peristaltic pump at a maximum pressure difference of 200 mm Hg for a suction period of 15 seconds or 20 seconds.

The results are summarized in Table 2.

TABLE 2

| Leaving Period | Suction Period | Recovered Serum | Hemolysis | Inserted Depth of Agglutinate Stopper |
|---|---|---|---|---|
| 5 min | 15 sec | 700 µl | None | 15.50 mm |
| 30 min | 15 sec | 1.5 ml | None | 19.15 mm |
| 60 min | 20 sec | 1.8 ml | None | 32.35 mm |

The suction filtration could be carried out without clogging the suction port port by agglutinate.

When the agglutination stopper was inserted into the whole blood after 60 minutes from drawing blood, the agglutination stopper sat on the gel, and agglutinate after the suction was very small: It was found that degeneracy proceeded in the thrombin type whole blood.

Example 4

Four 5 ml silica gel blood collecting tubes were provided, and 5 ml whole blood (hematocrit:43%) was placed in each blood collecting tube.

Using a plastic agglutinate stopper in the form of a cylinder 20 mm in diameter provided with nine holes 2 mm in diameter at the bottom, serum portion was filtered with removing agglutinate after 30 minutes, 60 minutes, 90 minutes and 120 minutes from drawing blood. The volum and hematocrit of the serum portion were measured. The above prefiltration device was attached onto a holder containing one sheet of polysulfone microporous membrane and two sheets of glass fiber, and filtration with pressure was carried out by combining a syringe instead of suction.

The results are shown in Table 3.

TABLE 3

| Leaving Period | Liquid Volume | Hct |
|---|---|---|
| 30 min | 1.4 ml | 7% |
| 60 min | 2.1 ml | 7% |
| 90 min | 2.1 ml | 7% |
| 120 min | 2.4 ml | 8% |

It was found that the serum portion volume increased with increasing leaving period but the hematocrit value was almost constant.

Example 5

Whole blood was drawn by a vacuum blood collecting tube from a healthy person, and serum was separated by the method similar to Example 1. In comparison, the same whole blood was centrifuged to separate serum. As to both sera, main biochemical assay items (23 items) were measured by an automatic clinical assay analyzer ("Hitachi 7170"), and the results are shown in Table 4.

TABLE 4

| Item | Unit | Filtration Serum | Centrifugation Serum |
|---|---|---|---|
| UA | mg/dl | 4.27 | 4.22 |
| TBil | mg/dl | 0.20 | 0.21 |
| BUN | mg/dl | 22.2 | 21.8 |
| Ca | mg/dl | 9.0 | 8.9 |
| TG | mg/dl | 49 | 49 |
| CRE | mg/dl | 0.82 | 0.83 |
| TCHO | mg/dl | 195 | 198 |
| Glu | mg/dl | 94 | 95 |
| TP | g/dl | 7.09 | 7.12 |
| Alb | g/dl | 4.15 | 4.16 |
| Alp | IU/L | 210 | 208 |
| AMYL | IU/L | 85 | 79 |
| CPK | IU/L | 83 | 83 |
| GGT | IU/L | 8 | 7 |
| GOT | IU/L | 13.5 | 13.7 |
| GPT | IU/L | 8.2 | 8.5 |
| LDH | IU/L | 135 | 135 |
| LAP | IU/L | 45 | 43 |
| CHE | IU/L | 292 | 297 |
| IP | IU/L | 3.6 | 3.6 |
| Na | mEq/L | 143.8 | 143.6 |
| K | mEq/L | 4.08 | 4.02 |
| Cl | mEg/L | 106.7 | 105.9 |

It was confirmed that, as to all items containing enzymes and electrolytes, there is no difference between the serum obtained by the method of the invention and the serum obtained by the centrifugation which causes a problem in clinical diagnosis, and both sera have equivalent quality.

What is claimed is:

1. A method of separating serum from a whole blood sample in which agglutinates of blood cells are formed, which comprises inserting a suction nozzle provided with an agglutinate stopper at a lower end into the whole blood sample located in a vessel at an insertion speed of 30 cm/sec or less, while keeping the suction pressure of the suction nozzle at 400 mm Hg or less, whereby the agglutinates of blood cells are substantially prevented from entering the suction.

2. The method of claim 1 wherein the agglutinate stopper has plural openings having a diameter of 100 µm to 5 mm.

3. The method of claim 1 wherein the agglutinate stopper is in a form of a plate with openings.

4. The method of claim 1 wherein the insertion speed is 10 cm/sec or less.

5. The method of claim 1 wherein the suction pressure is 200 mm Hg or less.

6. The method of claim 1 wherein the blood sample entering the suction nozzle is filtered by a glass fiber filter.

7. The method of claim 1 wherein the whole blood has been left for 1 to 120 minutes from the time of drawing blood.

* * * * *